United States Patent [19]

Spencer

[11] Patent Number: 5,674,333

[45] Date of Patent: Oct. 7, 1997

[54] TOTAL CONTAINMENT WELDING OF PLASTIC TUBES

[75] Inventor: Dudley W. C. Spencer, Wilmington, Del.

[73] Assignee: Denco, Inc., Wilmington, Del.

[21] Appl. No.: 399,339

[22] Filed: Mar. 6, 1995

Related U.S. Application Data

[63] Continuation-in-part of Ser. No. 158,505, Nov. 29, 1993, Pat. No. 5,397,425, which is a continuation-in-part of Ser. No. 965,875, Oct. 23, 1992, Pat. No. 5,279,685.

[51] Int. Cl.$^6$ .................................................. B32B 31/00
[52] U.S. Cl. .......................... 156/64; 156/158; 156/304.2; 156/304.6; 73/49.3; 73/52
[58] Field of Search .............................. 156/64, 158, 159, 156/304.2, 304.6; 73/46, 49.1, 49.3, 52

[56] References Cited

U.S. PATENT DOCUMENTS

| | | | |
|---|---|---|---|
| 3,853,655 | 12/1974 | Pecha | 156/159 |
| 4,306,447 | 12/1981 | Franks, Jr. | 73/46 |
| 4,719,687 | 1/1988 | Nanny | 73/49.1 X |
| 4,753,697 | 6/1988 | Shaposka et al. | 156/158 |
| 4,770,735 | 9/1988 | Shaposka et al. | 156/258 |
| 4,793,880 | 12/1988 | Shaposka e tal. | 156/158 |
| 4,832,773 | 5/1989 | Shaposka et al. | 156/158 |
| 4,864,101 | 9/1989 | Shaposka et al. | 219/243 |
| 4,897,138 | 1/1990 | Shaposka et al. | 156/158 |
| 4,913,756 | 4/1990 | Shaposka et al. | 156/158 |
| 4,933,036 | 6/1990 | Shaposka et al. | 156/158 |
| 5,141,592 | 8/1992 | Shaposka et al. | 156/515 |
| 5,143,568 | 9/1992 | Sheahan | 156/64 |
| 5,156,701 | 10/1992 | Spencer et al. | 156/158 |
| 5,158,630 | 10/1992 | Shaposka et al. | 156/158 |
| 5,209,800 | 5/1993 | Spencer et al. | 156/158 |
| 5,244,522 | 9/1993 | Spencer et al. | 156/158 |
| 5,248,359 | 9/1993 | Shaposka et al. | 156/158 |
| 5,256,229 | 10/1993 | Spencer | 156/158 |
| 5,279,685 | 1/1994 | Ivansons et al. | 156/158 |
| 5,285,678 | 2/1994 | McDaniel et al. | 73/49.3 |
| 5,397,425 | 3/1995 | Ivansons et al. | 156/503 |

*Primary Examiner*—David A. Simmons
*Assistant Examiner*—Paul M. Rivard
*Attorney, Agent, or Firm*—Connolly & Hutz

[57] ABSTRACT

Plastic tube sections are connected together by providing a pair of tubes each of which is inserted into the holder of a welding device in a bent condition so that each tube has a primary tube section and a secondary tube section with the primary tube sections being aligned with each other and the secondary tube sections aligned with each other. The tubes are heated by a wafer to create four separate tube sections which are then joined together in a dual weld wherein one of the welds joins the primary tube sections together and the other of the welds joins the secondary tube sections together. The welded primary tube sections are then separated from the secondary tube sections. Communication between each pair of tube sections is achieved by pressing the tube section open at the weld.

11 Claims, 4 Drawing Sheets

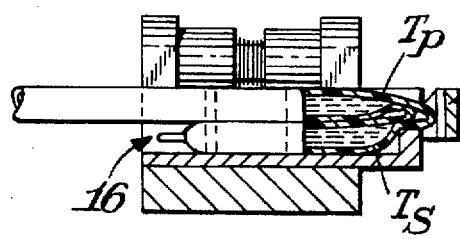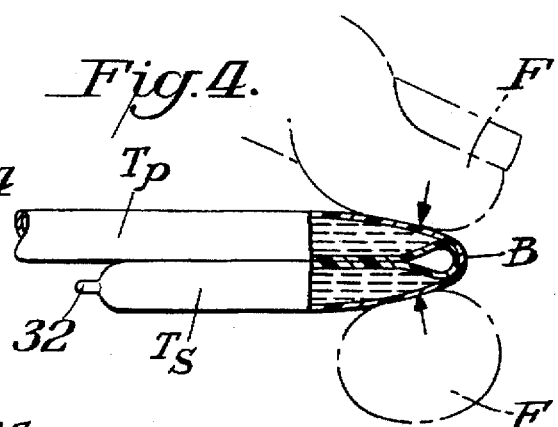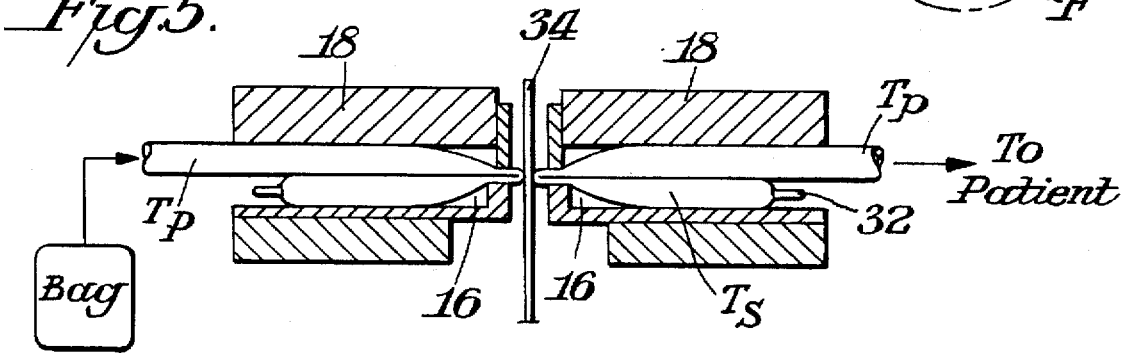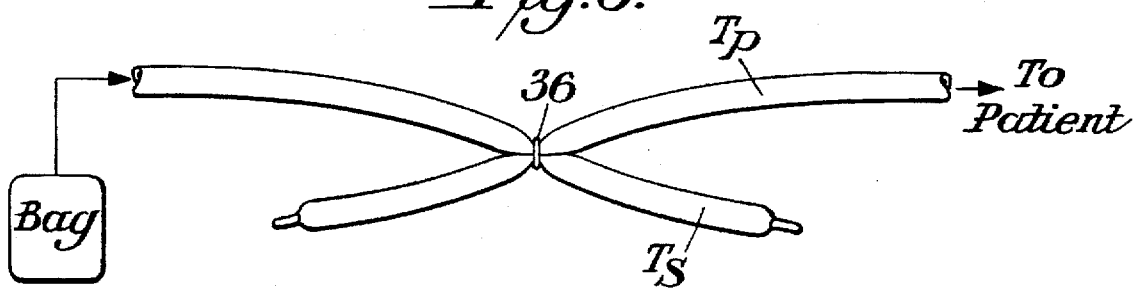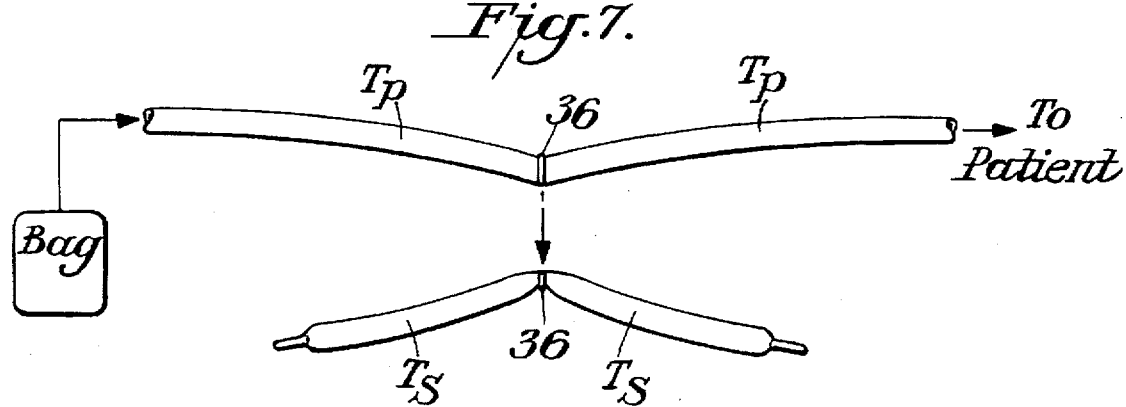

TOTAL CONTAINMENT WELDING OF PLASTIC TUBES

CROSS-REFERENCE TO RELATED APPLICATIONS

This application is a continuation in part of application Ser. No. 08/158,505 filed Nov. 29, 1993, now U.S. Pat. No. 5,397,425 which in turn is a continuation-in-part of application Ser. No. 07/965,875 filed Oct. 23, 1992, now U.S. Pat. No. 5,279,685.

BACKGROUND OF THE INVENTION

The present invention is directed to the sterile welding or disconnect procedures utilized, for example, in total containment welding of plastic tubes. Various patents of the assignee relate to devices which could be used for welding or disconnecting plastic tubes for various purposes. These patents include U.S. Pat. Nos. 4,753,697; 4,770,735; 4,793,880; 4,832,773; 4,864,101; 4,897,138; 4,913,756; 4,933,036; 5,141,592; 5,156,701; 5,158,630; 5,209,800; 5,244,522; 5,248,359; 5,256,229; and 5,279,685.

Among the uses of such types of devices is various medical purposes such as disclosed in the aforementioned patents. Where medical purposes are concerned there must be compliance with FDA requirements. This includes validating the strength and effectiveness of a weld where two plastic tubes are joined together in some manner other than simply a visual looking at the weld.

SUMMARY OF THE INVENTION

An object of this invention is to provide techniques whereby destructive testing could be done to welded plastic tubes in a manner that would confirm the strength of a weld simultaneously made between two primary tubes.

A further object of this invention is to provide various techniques which enhance the versatility of being able to take samples or insert various materials into tubes having other materials flowing therethrough.

In accordance with this invention a total containment welding device is utilized wherein the tube sections welded together are done in a technique wherein two individual tubes are placed in the device each in a bent condition. As a result, four tube sections are created in that each tube results in two tube sections because of the bend. Each pair of tube sections from one bent tube is aligned with a corresponding pair of tube sections from the other bent tube. The tubes are severed and each pair of aligned tube sections is welded together so that two welds are simultaneously produced. Since the welds are produced under identical conditions the characteristics of one weld would be the same as the characteristics of the other weld. This permits destructive testing to be done on one of the welded tube pairs which would be indicative of the strength of the weld on the other welded tube pairs.

The use of the bent tubes for creating two simultaneous welds is particularly advantageous in that it also permits a secondary welded tube to result which could be used for various purposes, such as to provide a sample of the materials flowing through the tubes. Additionally, these techniques permit a filter or other object to be inserted into the welded pair resulting in the welded pair resulting in the primary tube.

A BRIEF DESCRIPTION OF THE DRAWINGS

FIG. 3 is a cross sectional view taken through FIG. 1 along the line 3—3;

FIG. 4 is a front elevational view partly broken away showing a tube folded on itself and compressed to remove fluid from the bent portion;

FIG. 5 is a front elevational view of two clamped and bent tubes mounted in place to be double welded in accordance with this invention by use of the device of FIGS. 1–3;

FIG. 6 is a front elevational view showing a double welded tube formed by the device of FIGS. 1–5;

FIG. 7 is a front elevational view showing the double welded tube of FIG. 6 with the welds separated from each other;

DETAILED DESCRIPTION

The present invention is directed to techniques in the total containment welding of plastic tubes. These techniques involve use of the general type of device shown in parent application Ser. No. 08/158,505 filed Nov. 29, 1993, now U.S. Pat. No. 5,397,425, and in its parent application Ser. No. 07/965,875 filed Oct. 23, 1992, now U.S. Pat. No. 5,279,685 as well as U.S. Pat. No. 5,256,229. The details of these patents and application are incorporated herein by reference thereto. Accordingly, reference to the details of the device will be made where necessary or desired for an understanding of the present invention.

Figure 2:
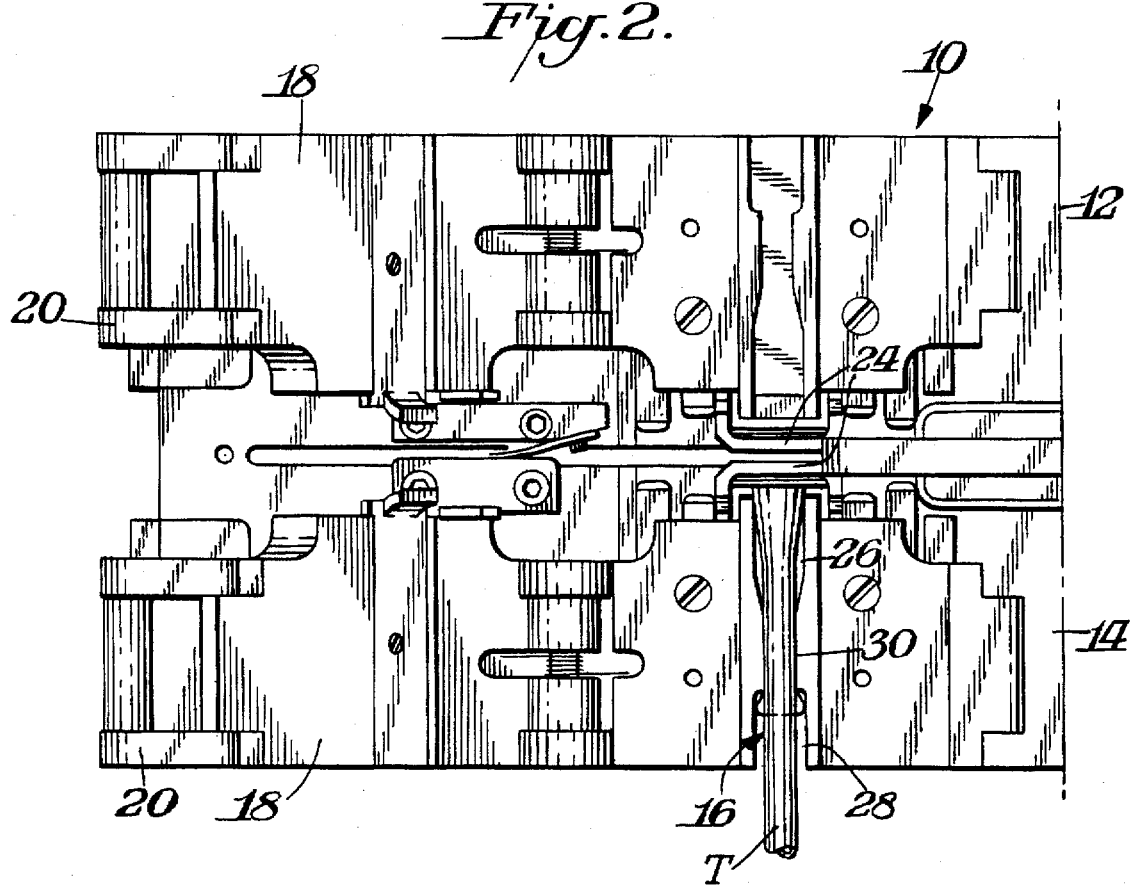
FIG. 2 is a top plan view of the welding device shown in FIG. 1.
Figure 1:
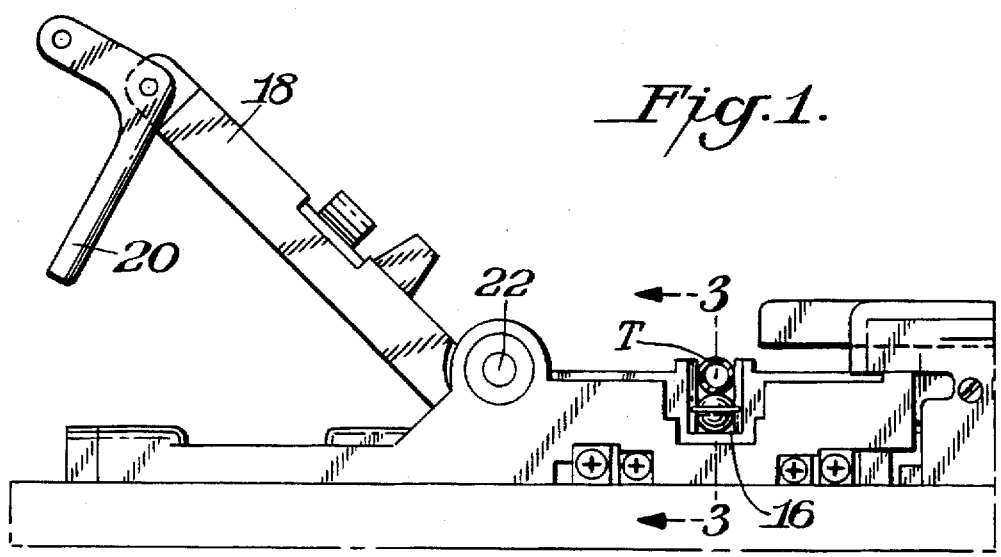
FIG. 1 is a side elevational view of a total containment welding device in accordance with this invention with the clamp in its open position.

As shown in FIGS. 1–3, the total containment welding device 10 includes a pair of tube holders 12,14. Each of the tube holders includes a tube receiving channel 16 into which a tube T is mounted. The tube is held in place by means of a clamp arm 18 having a manipulating handle 20. The clamp arm 18 is pivoted at pivot pin 22 for rotation into contact with tube T.

As best shown in FIGS. 3–5, tube T is inserted in its channel 16 by first bending the tube upon itself to create a primary tube section $T_p$ and a secondary tube section $T_l$. During the bending operation the tube is squeezed at the bight or area of the bend as shown in FIG. 4 by pressing the tube between the finger and thumb F,F so as to squeeze the fluid from the tube at the area of the bend as illustrated.

Each tube T is placed in its channel 16 in the manner illustrated in FIGS. 2 and 3 so that the bend B abuts against a stop member 24 at the end of its respective channel 16. Advantageously channel 16 is contoured to include a widened portion 26,28 at each end thereof with an intermediate narrow portion 30. See FIG. 2. Widened portion 26 is dimensioned to receive the tube at its bent portion B which is wider than the tube diameter because the tube has been compressed or flattened at that portion. Similarly, widened portion 28 is dimensioned to receive the flat weld seam 32 at the end of secondary tube $T_s$. Central portion 30 is dimensioned to conform in width to the diameter of the tube T where the tube is not in any flattened condition. By conforming the shape or width of the channel 16 to the physical characteristics of the bent tube, there is also further assurance of properly positioning each tube in its channel 16 so as to further assure a proper cutting or melting of the tubes at the bend B and then creating the double weld by use of device 10.

FIG. 5 illustrates the severing operation wherein a heated wafer 34 passes between the aligned tubes after the stop members 24 have been removed. The wafer melts each tube at the bend B thereby creating four individual tube sections. Two of the tube sections are aligned with each other and are indicated by the reference numeral $T_p$ to indicate that these tube sections when later welded together will form a primary tube. The other tube sections which comprise the bent end or stub of each tube are indicated by the reference numeral $T_s$ since these aligned tube sections will form a secondary tube when welded together.

By use of the techniques described in the parent patents and application, after the tube sections are severed at the bend B the four aligned tube sections are pushed into contact with each other while in a molten state thereby creating a weld 36. The weld 36 is more precisely a double weld which is clearly illustrated in FIG. 6 in that all four tube sections are welded together.

FIG. 7 illustrates the separation of the pair of tube sections $T_p$ from the pair of tube sections $T_s$ at the weld 36. Each weld 36 is of the same strength and has the same characteristics as the other weld 36 since both welds are simultaneously formed under the same conditions.

FIGS. 5-7 illustrate as one example in the use of the invention the forming of a primary tube which would connect a bag, such as a dialysate bag to a patient. Flow communication between the tube sections $T_p$ and $T_p$ is created by a squeezing at the weld 36 in the manner described in the parent patents and application. Similarly, flow communication would be achieved in the same manner between the secondary tube sections $T_s$ and $T_s$.

Since the weld 36 formed at the primary tube is formed under the same conditions as the weld 36 of the secondary tube both welds will have the same strength and characteristics. It is thereby possible to confirm and quantify the strength of weld 36 for the primary tube by performing tests on the weld 36 of the secondary tube even where such tests are of a destructive nature. This is because both welds are made at the same time, temperature, compression, spacing, etc. Statistical comparison testing establishes weld equivalence.

Once the weld equivalence is established the stub end or secondary tube $T_s$ can be subjected to the various destructive tests to qualify the integrity of the main line or primary tube $T_p$. These tests may include, for example, pressure, tensile, bending, cell damage, flow rates. For in process immediate validation the stub weld can be bent 180° and pressure tested to 50 psi (clamping). This test is severe, and will immediately test for weld integrity.

The following is an example of on-line testing protocol.

1. Immediately after making a weld, drop the detached weld sample to be tested into a polyethylene bag and heat seal open end of the bag. This makes a hermetically sealed pouch, with the weld sample inside. A zip-lock bag would also suffice.

2. Grasp the corner of the bag, place the weld sample into the jaws of a vise so that the weld is visible at the vise jaw face.

3. Activate the vise, bringing the fluid pressure inside the tube (and weld) to 50 lbs/in$^2$ pressure, hold for 5 seconds.

4. Observe the weld for pin-hole leaks or other signs of failure.

5. If the test is satisfactory, discard the test sample and release the main seal and its contents for use.

6. If the test sample fails, reject main seal and remove bent-tube welder from service immediately.

The following is a comparison of the primary and secondary weld strengths using the bent tube sterilely connection technology of the techniques of this invention.

Comparison of primary and secondary weld strengths using the Bent-tube sterile connection technology The Primary and secondary welds are sterilely connected at the identical time and under identical conditions, therefore, both welds are mirror images of each other.

Sealing wafer temperature: 320° C.

Exposure time: 1 second

Tensile test Unwelded tube=9.5 kg±0.5 kg

| Tensile test Primary Weld kg | % weld strength to unwelded tubes | Secondary Weld kg. |
|---|---|---|
| 7.1 | 74 | 7.15 |
| 7.2 | 75 | 7.1 |
| 6.95 | 72 | 6.93 |
| 7.0 | 73 | 7.1 |
| 7.15 | 75 | 7.1 |
| 7.0 | 73 | 6.95 |
| 7.1 | 74 | 7.15 |
| 7.0 | 73 | 6.97 |
| 7.1 | 74 | 7.0 |
| 6.95 | 73 | 7.0 |

Internal Pressure test 3.5 kg/cm$^2$ and 7.0 kg/cm$^2$ (Measured by pressure gauge; Pass or Fail)

| Primary Weld | | Secondary Weld | |
|---|---|---|---|
| 3.5 kg/cm2 | 7.0 kg/cm2 | 3.5 kg/cm2 | 7.0 kg/cm2 |
| P | P | P | P |
| P | P | P | P |
| P | P | P | P |
| P | P | P | P |
| P | P | P | P |
| P | P | P | P |
| P | P | P | P |
| P | P | P | P |
| P | P | P | P |
| P | P | P | P |
| 50 lbs/in2 | 100 lbs/in2 | 50 lbs/in2 | 100 lbs/in2 |

Internal Pressure test
(Measured by tube diameter expansion; Original tube outside diameter=4.0 mm)

By squeezing the tube flat, in the jaws of a vise, leaving the weld exposed beyond the vise jaws, both the primary and secondary welds remain sound when the tube diameter expands to 5.0 mm or 20% increase in size. This equates to an internal pressure of 150 lbs/in2 or 15 kg/cm2.

Unwelded tube burst strength is 200 lbs/in2.

Similarly, if one squeezes the tube sample by finger and thumb pressure, while the sample is in a zip-lock bag, the tube diameter will increase from 4.0 mm to 4.3 mm which equates to an internal pressure of 50lbs/in2 or 5.5kg/cm2. For most applications a simple finger and thumb test would be adequate to demonstrate weld integrity of the secondary weld, and thus establish quality assurance of the primary weld.

This aspect of the invention thus broadly involves simultaneously creating two welds from two pair of tube sections under identical conditions by any manner of welding. As a result the testing of one weld will be indicative of the characteristics of the other weld.

Figure 8:
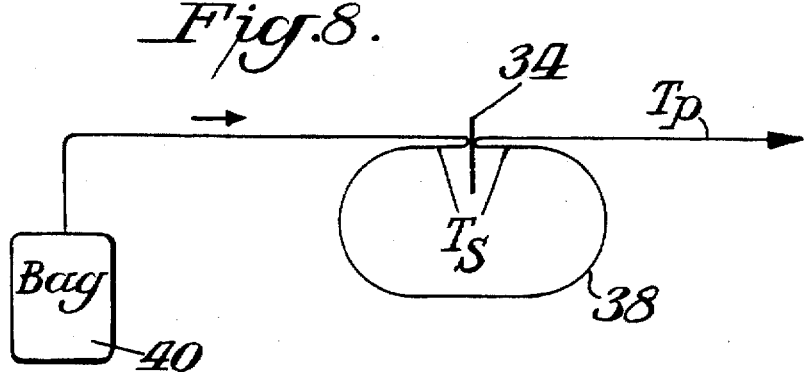
FIG. 8 is a schematic view showing use of the invention for creating a sealed closed loop sample tube.

The present invention not only permits the effective testing of a primary tube weld, but also permits the increase in versatility in altering the primary tube. FIG. 8 illustrates a practice of the invention wherein a single tube is bent so that a loop 38 is created between the bends to form secondary tube sections $T_s$. The tube is severed at the bends as illustrated by the passing of the wafer 34. After the wafer has passed the aligned tube sections are pressed together so that a primary tube $T_s$ is created by one of the welds and a secondary tube $T_s$ is created in the form of the loop 38. The loop 38 may thus function as a sample which could be retained for further testing. For example, the invention in the techniques illustrated in FIG. 8 may be used in connection with the flow of blood. When blood is drawn from a donor there is an important need to determine the blood quality without compromising the blood or its container. This can be done in the manner illustrated in FIG. 8 where the sample is in loop 38. The main tube contents would remain in the primary tube $T_p$ without being disturbed while the sample is examined.

Figure 9:
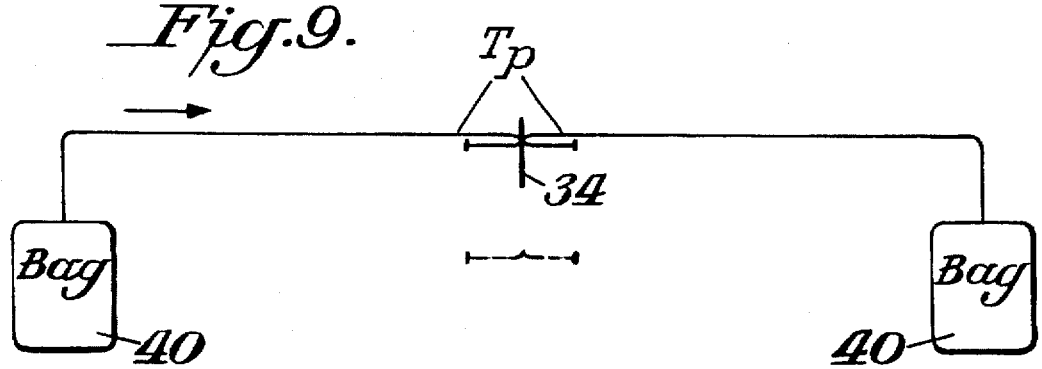
FIG. 9 is a schematic view showing use of the invention for creating a straight sealed sample tube.

FIG. 9 illustrates a practice of the invention wherein a tube from one bag 40 is to be joined to a tube from a second bag 40 with the creation of a sample tube. This is accomplished by bending the tube from each bag as illustrated wherein the wafer 34 passes between the bent tubes and thereafter the aligned primary tubes $T_p$ leading from each bag are connected together while a sample is connected from the welded stub ends, as shown in phantom.

The techniques of FIG. 9 could be used, for example, to create a transfer in a closed system where the red cells are transferred but not the white cells.

Figure 10:
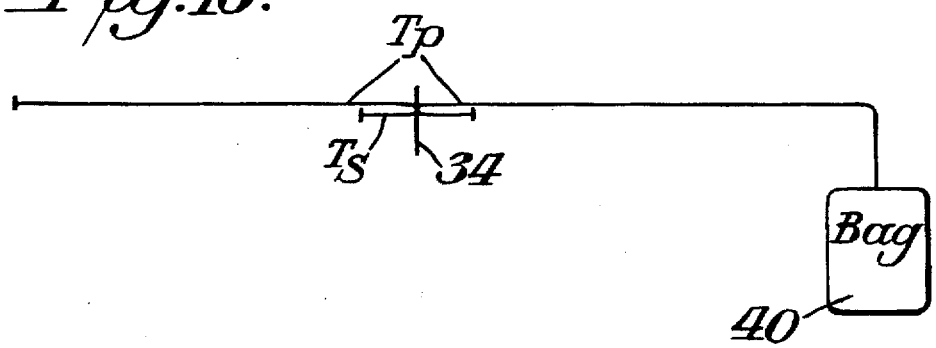
FIG. 10 is a schematic view showing use of the invention for increasing the length of a primary tube.

FIG. 10 illustrates a practice of the invention wherein it is desired to increase the length of the tube extending from bag 40. This is accomplished by bending the tube and inserting the bent tube in the device juxtaposed a second tube which is also bent. After the wafer 34 passes through the tubes and the aligned sections are joined together a primary tube $T_p$ is created of increased length with a sample tube $T_s$ being created from the welded stub ends.

The techniques of FIG. 10 could also be used to introduce additional elements from the newly added tube section such as nutrients, conditioners, neutralizers and reagents.

Figure 11:
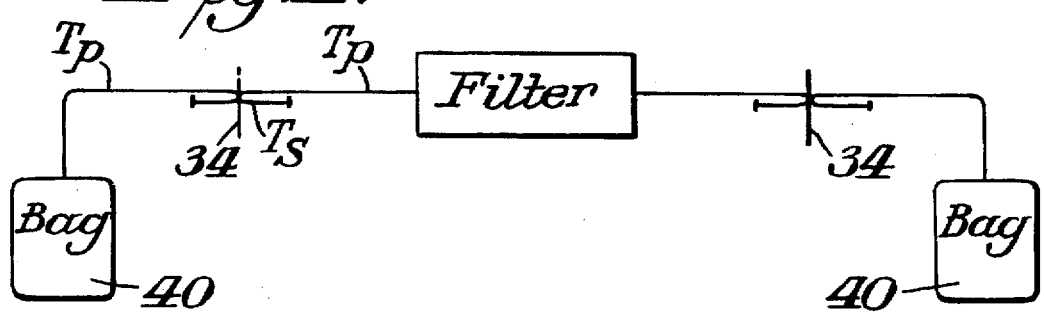
FIG. 11 is a schematic view showing use of the invention for inserting a filter into the primary tube.

FIG. 11 illustrates a practice of the invention wherein it is desired to measure the effectiveness of filters, mixers storage or for example conditioners. As illustrated therein, two welding deices would be used. A tube leading from one bag 40 is bent and inserted in one device with a tube leading from a filter being bent and inserted in that device. The other bent end leading from the filter is inserted in the second device as is the tube from the other bag 40. The primary tube $T_p$ from the filter is welded to its aligned primary tube $T_p$ from each respective bag after passage of the wafer 34 of each device. This also results in the creation of two secondary tubes $T_s$.

The practice of the invention of FIG. 11 provides flexibility to hospitals and doctors and permits the saving of inventory by having an instant splice. This avoids the need for certain sterilizations. One of the bags could be used for white cells while, for example, a leucocyte could be introduced in the added section connected to the filter.

Figure 12:
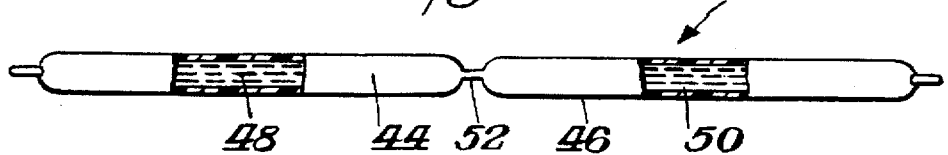
FIG. 12 is a side view partially broken away and in section showing a material containing tube which is intended to be inserted into a primary tube in accordance with this invention for adding the materials to the primary tube.
Figure 13:
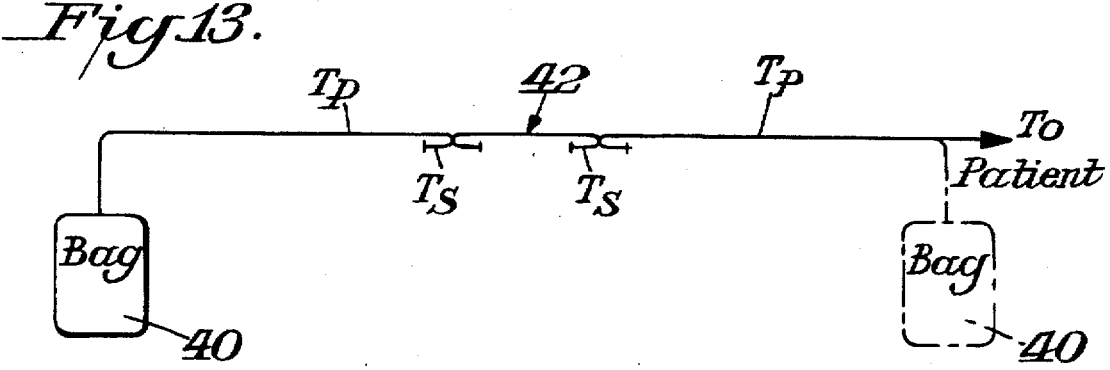
FIG. 13 is a schematic view showing use of the invention for connecting the tube of FIG. 12 to a primary tube.

FIGS. 12–13 show an alternative manner of using the invention for the introduction of various elements. As shown in FIG. 12, for example, tube 42 is provided having a pair of chambers 44,46 each filled with a separate component 48,50. The sections 44,46 are sealed from each other by seal 52. When it is desired to introduce these components into a primary tube, the seal 52 is broken by, for example, squeezing the seal so that there is flow communication between the components 48,50 in the resultant tube 42. Each end of tube 42 is then bent and inserted in an appropriate device (such as device 10 of FIGS. 1–3) in line with a primary tube leading from a bag 40 or the patient. By using the previously described techniques the two primary tubes $T_p,T_p$ are put in flow communication with the tube insert 42 and secondary tubes $T_s$ are also created. In this manner, it is thereby possible to have components, such as two part pharmaceuticals, reagent chemicals, epoxys, food additives, or preservatives introduced from tube 42 into the primary tube $T_p$.

The practices of FIGS. 11 and 12–13 permits the introduction of various components, such as blood, beer, wine, mixers, storage conditioners, etc. into a primary tube for various types of purposes not limited to medical uses.

It is therefore to be understood that the present invention while directed primarily to total containment welding may have other uses including industrial uses unrelated to medical purposes.

What is claimed:

1. A method of testing the weld characteristics of a pair of primary tubes welded together comprising welding two primary tube sections together and two secondary tube sections together in a double weld made from heat softened tube sections pressed together under the same conditions including at the same time, temperature, compression and spacing conditions; each of the secondary tube sections having a welded sealed closed end; separating the double weld into a weld of the two primary tube sections and a weld of the two secondary tube sections; opening communication between the two primary tube sections and between the two secondary tube sections; and performing tests on the characteristics of the weld for the combined secondary tube sections having sealed remote ends to thereby indicate the comparable characteristics of the weld in the primary tube sections.

2. The method of claim 1 wherein each tube is inserted in a channel of a tube holder in a condition bent with the bent end exposed from the channel to form two sets of aligned tube sections; and forming the primary tube from one set of aligned tube sections and the secondary tube from the other set of aligned tube sections.

3. The method of claim 2 wherein the welds are formed by a melt/wipe technique.

4. A method of creating a primary tube and a secondary tube comprising the steps of placing a first plastic tube in a bent condition in one holder of a welding device and placing a second plastic tube in a bent condition in a second holder of the welding device generally juxtaposed the tube in the first holder, each of the plastic tubes having a sealed closed end, the placing of the bent tubes causing the sealed closed ends of the plastic tubes to generally aligned with each other, severing the tubes at the area of each bend to create two sets of aligned tube sections which are heated to become soft, pressing each set of aligned heat softened tube sections together, simultaneously creating a dual weld from the two sets of aligned heat softened tube sections to create a primary tube from one set and a secondary tube from the other set, separating the dual weld to separate the welded primary tube from the welded secondary tube, the resultant secondary tube having one of the welded sealed closed ends at each end of the secondary tube with the weld separating the interior of the secondary tube into two separate closed chambers, the resultant primary tube having two separate chambers separated by the weld at the primary tube, and opening communication of the two separate chambers of the primary tube at the weld of the primary tube by popping open the weld of the primary tube.

5. The method of claim 4 wherein the first plastic tube and the second plastic tube are initially integral and are bent to form the two sets of tube sections, joining the secondary tube sections together by the weld to form a closed loop.

6. The method of claim 4 wherein the first tube and the second tube are initially separate from each other, and the secondary tube sections are welded together to form a single sample tube.

7. The method of claim 4 wherein one of the primary tube sections is connected to a bag and the other of the primary tube sections extends the overall length of the combined primary tube sections.

8. The method of claim 7 wherein the extended primary tube section includes additional components which are permitted to flow into the combined primary tube sections.

9. A method of creating a primary tube and a secondary tube comprising the steps creating placing a first plastic tube in a bent condition in one holder of a welding device and placing a second plastic tube in a bent condition in a second holder of the welding device generally juxtaposed the tube in the first holder severing the tubes at the area of each bend to create two sets of aligned tube sections, pressing each set of aligned tube sections together, simultaneously creating a dual weld from the two sets of aligned tube sections to create a primary tube from one set and a secondary tube from the other set, separating the dual weld to separate the welded primary tube from the welded secondary tube, opening communication of the primary tube at the weld of the primary tube, and a second welding device is used to connect a further primary tube section with one of the primary tube sections whereby three primary tube sections are connected together which include a central primary tube section.

10. The method of claim 9 wherein the central primary tube section includes an added component.

11. The method of claim 10 wherein the central section includes a tube having two chambers separated from each other with each chamber having a different component, and opening communication between the chambers immediately prior to joining the central primary tube section to the other primary tube sections.

* * * * *